United States Patent [19]

Petzoldt et al.

[11] 4,011,314
[45] Mar. 8, 1977

[54] 7-HYDROXYESTRADIOLS

[75] Inventors: Karl Petzoldt; Hans-Jörg Vidic; Klaus Prezewowsky; Yukishige Nishino; Rudolf Wiechert; Henry Laurent, all of Berlin, Germany

[73] Assignee: Schering Aktiengesellschaft, Berlin & Bergkamen, Germany

[22] Filed: Oct. 9, 1975

[21] Appl. No.: 621,136

[30] Foreign Application Priority Data

Oct. 14, 1974 Germany .......................... 2449327
Aug. 8, 1975 Germany .......................... 2535997

[52] U.S. Cl. ..................... 424/241; 260/239.55 R; 260/397.5; 260/397.4; 195/51 S
[51] Int. Cl.² ..................... A61K 31/58; C07J 1/00
[58] Field of Search ............... 260/397.5, 239.55 R

[56] References Cited

UNITED STATES PATENTS 3,115,444  12/1963  Laskin et al. .................... 195/51

Primary Examiner—Elbert L. Roberts
Attorney, Agent, or Firm—Millen & White

[57] ABSTRACT

7-Hydroxyestradiols of the formula

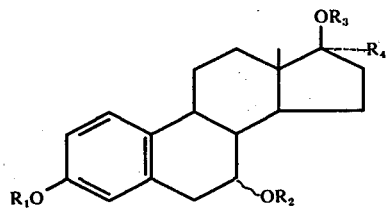

wherein $R_1$ is hydrogen, acyl, alkyl, cycloalkyl, an oxygenated saturated heterocyclic group or hydrocarbylsulfonyl; $R_2$ and $R_3$ each are hydrogen, acyl, oxygenated saturated heterocyclic group or $R_2$ is hydrocarbylsulfonyl and $R_4$ is alkyl, alkenyl, chlorinated alkenyl, alkynyl or chlorinated alkynyl, are useful for treating estrogen deficiency symptoms.

28 Claims, No Drawings

7-HYDROXYESTRADIOLS

BACKGROUND OF THE INVENTION

This invention relates to novel 7-hydroxyestradiols and to their use in treating estrogen deficiency syndromes in post-menopausal females.

SUMMARY OF THE INVENTION

In a composition aspect, this invention relates to novel 7-hydroxyestradiols of the general Formula I

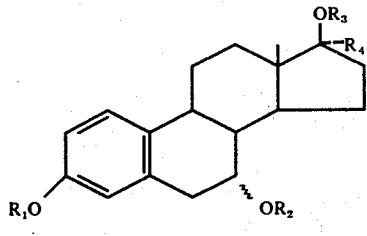

wherein $OR_2$ is in the α- or β-position, $R_1$ is a hydrogen atom, the acyl radical of a carboxylic or sulfonic acid, alkyl, cycloalkyl, or an oxygen-containing, saturated heterocyclic group; $R_2$ and $R_3$, which can be alike or different, each are a hydrogen atom, the acyl radical of a carboxylic or sulfonic acid, or an oxygen-containing, saturated heterocyclic group; and $R_4$ is alkyl, alkenyl, chlorinated alkenyl, alkynyl or chlorinated alkynyl.

In another composition aspect, this invention relates to pharmaceutical compositions comprising a compound of this invention.

In process aspects, this invention relates to processes for making and using the compositions of this invention.

DETAILED DESCRIPTION

Examples of $R_1$, $R_2$ and $R_3$ acyl groups are the physiologically acceptable acyl groups of acids conventionally employed for the esterification of steroid alcohols. Preferred are acyl groups of hydrocarbon carboxylic acids and hydrocarbon sulfonic acids, each of 1-15 carbon atoms. Especially preferred as acyl groups are alkanoyl and alkanesulfonyl of 1-7 carbon atoms, e.g., the acyl radical of formic acid, acetic acid, propionic acid, butyric acid, isobutyric acid, valeric acid and enanthic acid, and of methanesulfonic, ethanesulfonic, propane- and isopropanesulfonic and butanesulfonic acid. Although alkanoyl and alkanesulfonyl of 1-7 carbon atoms are especially preferred, $R_1$ and $R_3$ acyl groups contemplated as equivalents are those of the above formula wherein $R_1$, $R_2$ and $R_3$ each are the acyl group of another organic hydrocarbon carboxylic acid, e.g., especially an aliphatic carboxylic acid, e.g., an alkanoic acid of 8-12 carbon atoms, which can be unsaturated, branched, polybasic, or substituted in the usual manner, for example, by hydroxy or halogen atoms; a cycloaliphatic, aromatic and mixed aromatic-aliphatic (alkaryl and aralkyl) acid, which can likewise be substituted in the usual manner; examples of such equivalent acids being caproic acid, enanthic acid, undecyclic acid, oleic acid, dichloroacetic acid, cyclopentylpropionic acid, phenylpropionic acid, phenylacetic acid, phenoxyacetic acid, succinic acid, benzoic acid; others being acids containing 1-18, preferably 2-12 carbon atoms, including an aliphatic acid containing 1-18, preferably 1-6 carbon atoms, e.g., α-ethylvaleric, 2-ethylbutyric, 3-ethylbutyric, hexanoic, diethylacetic, triethylacetic, enanthic, octanoic, undecyclic and palmitic acid; a cyclic acid, preferably a cycloaliphatic acid, containing, e.g., 5-18 carbon atoms, e.g., cyclopropylideneacetic, cyclobutylcarboxylic, cyclopentylcarboxylic, cyclopentylacetic, β-cyclopentylpropionic acid, cyclohexylacetic, cyclohexylacetic and β-cyclohexylpropionic acid; a carbocyclic aryl or alkaryl acid, e.g., containing 6-18 carbon atoms, and 1 to 5, preferably 1 or 2 rings, e.g., benzoic, 2-, 3-, or 4-methylbenzoic, 2,3-, 2,4-, 2,5- 2,6-, 3,4- and 3,5- dimethylbenzoic, ethylbenzoic, 2,3,6-trimethylbenzoic and 3-methyl-α-naphthoic acid; an aralkyl acid, e.g., containing 7-18 carbon atoms, e.g., β-phenylpropionic, a polybasic acid, e.g., containing 2-18 carbon atoms and 1 to 5 hydroxy groups, e.g., glycolic, lactic, citric, tartaric, d-maleic, d-glyceric, and salicyclic acid; and the corresponding acids containing one, two or more of simple substituents, e.g., halo, alkoxy, acyloxy, etc., in the molecule, e.g., chloroacetic, fluoroacetic, trichloroacetic, trifluoroacetic, 2,3,4-trimethoxybenzoic, phenoxyacetic, α-naphthoxyacetic acid.

Contemplated as equivalents of the acyl radicals of alkanesulfonic acids are those of other aliphatic, cycloaliphatic, and aromatic sulfonic acids of 1-15 carbon atoms. Such equivalent aliphatic sulfonic acids can be substituted, for example, by halogen, e.g., chlorine, or by an amino group. The following aliphatic sulfonic acids are exemplary of such contemplated equivalents as the acyl radicals of cyclopentane- and cyclohexanesulfonic acids, benzensulfonic acid, p-toluenesulfonic acid, and p-chlorobenzenesulfonic acid, as well as N,N-disubstituted aminosulfonic acids., e.g., wherein the two substituents are alkyl of 1-6 carbon atoms or alkylene of 4—6 members optionally interrupted by a hetero atom, such as nitrogen, oxygen, or sulfur, e.g., N,N-dimethylaminosulfonic acid, N,N-diethylaminosulfonic acid, N,N-bis(=-chloroethyl)aminosulfonic acid, N,N-diisobutylaminosulfonic acid, N,N-dibutylaminosulfonic acid, pyrrolidino-, piperidino-, piperazino-, N-methylpiperazino-, and morpholinosulfonic acids.

Examples of $R_4$ hydrocarbyl groups are alkyl of 1-5 carbon atoms, alkenyl or alkinyl of 2-5 carbon atoms, e.g., methyl, ethyl, propyl, butyl, pentyl, vinyl, ethynyl, chloroethynyl, propynyl, and butadiynyl. The alkenyl and slkynyl groups can also be substituted by chlorine. Preferred $R_4$ groups are ethynyl and chloroethynyl.

Preferred $R_1$ alkyl groups are alkyl of 1-5 carbon atoms, including methyl, ethyl and isopropyl. Contemplated equivalents are alkyl groups bearing one or more substituents, e.g., halogen atoms or lower alkoxy, e.g., methoxyethyl, chloromethyl, methoxy, butyl and bromoethyl. Especially preferred are the methyl and ethyl groups.

Cycloalkyl of 3-8 carbon atoms are appropriate substituents for $R_1$, but cyclopentyl is preferred.

Oxygen-containing heterocyclic residues included within the definition of $R_1$, $R_2$ or $R_3$ are those derived from heterocycles with at least one oxygen atom in the ring and in a completely saturated oxygen-atom-containing ring. Tetrahydrofuryl and tetrahydropyranyl residues are preferred, most particularly tetrahydropyranyl.

Thus, a preferred aspect of this invention relates to novel compounds of general Formula Ia

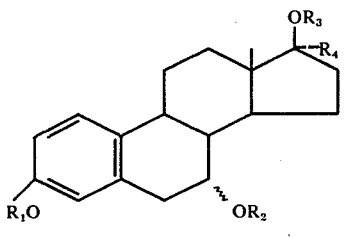

wherein $R_1$ is a hydrogen atom, the acyl radical of a hydrocarbon carboxylic or sulfonic acid of 1–15 carbon atoms, alkyl of 1–8 carbon atoms, cycloalkyl of 3–7 carbon atoms, tetrahydrofuranyl or tetrahydropyranyl;

$R_2$ and $R_3$ each are a hydrogen atom, the acyl radical of a hydrocarbon carboxylic or sulfonic acid of 1–15 carbon atoms, tetrahydrofuranyl or tetrahydropyranyl; and $R_4$ is alkyl, alkenyl, chloroalkenyl, alkynyl or chloroaklynyl, each of up to 5 carbon atoms.

Compounds preferred in accordance with this invention include:

a. 7-hydroxyestradiol of Formula I, wherein $R_1$, $R_2$ and $R_3$ each are hydrogen or alkanoyl of 1–7 carbon atoms, the 7-hydroxy is in the α-position and $R_4$ is vinyl, ethynyl or chloroethynyl;

b. 7-hydroxyestradiol of Formula I, wherein $R_1$, $R_2$ and $R_3$ each are hydrogen or alkanoyl of 1–7 carbon atoms, the 7-hydroxy is in the β-position and $R_4$ is vinyl, ethynyl or chloroethynyl;

c. 7-hydroxyestradiol of Formula I, wherein $R_1$ is cycloalkyl of 3–8 carbon atoms, $R_2$ and $R_3$ each are hydrogen or alkanoyl of 1–7 carbon atoms and $R_4$ is vinyl, ethynyl or chloroethynyl;

d. 7-hydroxyestradiol of Formula I, wherein R and $R_2$ each are hydrogen, tetrahydropyranyl or tetrahydrofuryl, $R_3$ is hydrogen or alkanoyl of 1–7 carbon atoms and $R_4$ is vinyl, ethynyl or chlorethynyl;

e. 7-hydroxyestradiol of Formula I, wherein $R_1$ and $R_2$ each are hydrogen, alkanoyl of 1–7 carbon atoms or alkanesulfonyl of 1–4 carbon atoms; $R_3$ is hydrogen, alkanoyl of 1–7 carbon atoms, tetrahydrofuryl or tetrahydropyranyl; and $R_4$ is vinyl, ethynyl or chloroethynyl; and f. 7-hydroxyestradiol of Formula I, wherein $R_1$ is hydrogen or alkyl of 1–5 carbon atoms and $R_4$ is vinyl, ethynyl or chloroethynyl.

The compounds of this invention have an advantageous, associated pharmacological activity. On the basis of the strongly vaginotropic and weakly uterotropic effectiveness, they are preferably suitable for the treatment of female patients in the post menopause. Thus, the compounds can be utilized for the treatment of estrogen deficiency syndromes wherein a centrally controlled effect on the uterus is to be avoided, but wherein an effect on the vagina is desirable. The compounds of this invention are furthermore also suitable as intermediates for the preparation of pharmacologically valuable steroids, such as equilin.

The favorable estrogenic dissociation can be proven, for example, by conducting the sialic acid test on mice, after oral as well as subcutaneous administration.

Thus, the compounds of this invention, as demonstrated in Table 1 using as example 17α-ethynyl-1,3,5(10)-estratriene-3,7α,17 β-triol, show a dissociation quotient far exceeding that of the standard substances estradiol and 17α-ethynylestradiol.

TABLE 1

| Compound | Threshold Vale [mg.] p.o. | Relative Effectiveness | | Dissociation Quotient p.o. |
| --- | --- | --- | --- | --- |
| | | Vaginotropic | Uterotropic | |
| Estradiol | 0.05–0.1 | 1 | 1 | 1 |
| 17α-Ethynyl-estradiol | 0.01 | 9.1 | 10.9 | 0.9 |
| 17α-Ethynyl-1,3,5(10)-estratriene-3,7α,17β-triol | 0.03 | 0.898 | 0.099 | 9.1 |

The sialic acid test is conducted as follows:

The mice are ovariectomized. Starting with the tenth day after castration, the animals receive the substance to be tested once daily p.o. for 3 days. On the fourth day, the animals are sacrificed. Vagina and uterus are immediately excised and weighed into a test tube for hydrolysis. The determination of the sialic acid is conducted according to Svennerholm [Biochem. Biophys. Acta 24 (1957) 604 ]. The dose-dependent increase in the organ weights of vagina and uterus, as well as the reduction in sialic acid content are determined, and the relative strength of activity of the substance to be tested as compared to the standard substance estradiol is thus found. The relative effectiveness values are correlated, resulting in the degree of dissociation Q. For the standard compound estradiol, Q = 1. Compounds with Q > 1 are relatively vaginotropic, those with Q < 1 are relatively uterotropic.

The threshold values indicated in Table 1 were determined in the usual Allen-Doisy test on rats. The invention furthermore also relates to medicinal agents containing 7-hydroxyestradiols of general Formula I as the active ingredient.

The special drug preparations are produced in the usual manner by converting the active agents together with the vehicles, diluents, flavor-ameliorating agents, etc. customary in galenic pharmacy into the desired form of application, such as tablets, dragees, capsules, solutions, etc. The concentration of effective agent in the thus-formulated medicinal compositions is dependent on the form of administration. Thus, a tablet preferably contains 0.01 – 10 mg.; solutions for parenteral application contain 0.1 – 20 mg./ml. of solution.

Oral administration is preferred, the compounds of this invention being particularly valuable in the treatment of female mammals afflicted with estrogen dificiency syndrome. In this regard, they can be employed in substantially the same way as the known compound 17α-ethynyl-estradiol.

Vehicles usable for the compounds of this invention include conventional excipients, i.e., pharmaceutically acceptable organic or inorganic carrier substances suitable for parenteral, enteral or topical application which do not deleteriously react with the active compounds. Suitable pharmaceutically acceptable carriers include but are not limited to water, salt solutions, alcohols, vegetable oils, polyethylene glycols, gelatine, lactose, amylose, magnesium stearate, talc, silicic acid, viscous paraffin, perfume oil, fatty acid monoglycerides and diglycerides, pentaerythritol fatty acid esters, hydroxy methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

For parenteral application, particularly suitable are solutions, preferably oily or aqueous solutions, as well as suspensions, emulsions, or implants, including suppositories. Ampoules are convenient unit dosages.

For enteral application, particularly suitable are tablets, dragees, or capsules having talc and/or a carbohydrate carrier or binder or the like, the carrier preferably being lactose and/or corn starch and/or potato starch. A syrup, elixir or the like can be used wherein a sweetened vehicle is employed. Sustained release compositions can be formulated including those wherein the active compound is protected with differentially degradable coatings, e.g., by microencapsulation, multiple coatings, etc.

The dosage of the medicinal agents of this invention can vary, depending on the form of application and the respectively selected compound. Moreover, the dosage can change from one patient to the next. In general, the compounds of this invention are administered in a concentration capable of providing effective results, that is, amelioration of the symptoms of estrogen deficiency in the afflicted female mammal, without causing any disadvantageous or damaging side effects whatever; thus, the compounds are administered, for example, at a dosage level ranging from approximately 0.02 mg. to approximately 20 mg., although changes can be made under certain circumstances, so that a dosage level of more than 20 mg., e.g. up to 50 mg., is employed. However, a dosage level in the range from about 0.05 mg. to about 5 mg. is preferably employed.

The invention furthermore relates to a process for the preparation of the 7-hydroxyestradiols of general Formula I, characterized in that (a) a 7-hydroxyestrone of general Formula II

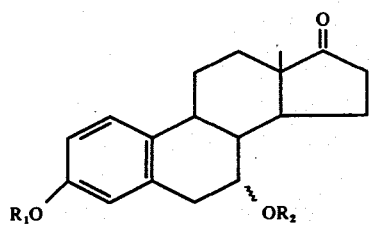

wherein $R_1$ and $R_2$ have the above-indicated meanings, is alkylated according to conventional methods; an unsaturated 17α-alkyl group is optionally hydrogenated and, depending on the lastly desired meanings of $R_1$, $R_2$ and $R_3$ in the final product, ether or acyl groups are optionally split off and/or free hydroxy groups are etherified and/or esterified; or (b) for preparing 7α-$OR_2$ compounds of general Formula I, a 17α-$R_4$-estradiol of general Formula III

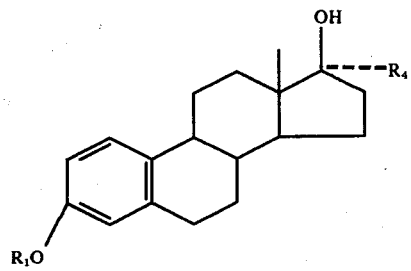

wherein $R_1$ and $R_4$ have the above-indicated meanings, is fermented with a fungal culture of the genera Absidia, Aspergillus, Rhizopus, Pellicularia, or Diplodia, and, depending on the lastly desired meanings of $R_1$, $R_2$ and $R_3$ in the final product, optionally one or several hydroxy groups are etherified and/or esterified.

The alkylation can take place according to conventional methods with an organometallic compound wherein the organic residue represents $R_4$ and which can be an alkyl magnesium halide, e.g. methylmagnesium bromide or iodide, an alkenyl magnesium and/or alkenyl zinc halide, e.g. vinylmagnesium bromide or allylmagensium bromide, an alkinyl magnesium halide, e.g. ethynylmagnesium bromide, propynylmagnesium bromide, or propynylzinc bromide, or an alkali metal acetylide, such as potassium acetylide. The organometallic compound utilized as the alkylating agent can also be formed in situ and made to react with the 17-ketone of Formula II. Thus, for the reaction with organometallic alkinyl compounds, the ketone is treated in a suitable solvent, with an alkyne, chloroalkyne, or alkadiyne, and an alkali metal, preferably in the presence of a tertiary alcohol or ammonia, optionally under elevated pressure. The unsaturated 17α-alkyl residues can be converted, by hydrogenation- into the corresponding 17α-alkenyl and/or saturated 17α-alkyl steroids. The hydrogenation is, as conventional, conducted preferably by reacting steroids having an unsaturated 17α-alkyl residue with hydrogen in the presence of a hydrogenation catalyst. Examples for suitable hydogenation catalysts are palladium catalysts or platinum oxide catalysts, optionally on supports.

7α-OH compounds of general Formula I can also be obtained from 17α-$R_4$-estradiol of the general Formula III by a microbiological method. The 7α-hydroxylation is accomplished with the use of fungal cultures of the genera Absidia, Aspergillus, Rhizopus, Pellicularia, and Diplodia. Suitable strains are, for example:

Absidia orchidis (ATCC 8990)
Aspergillus luchuensis (CBS)
Rhizopus nigricans (ATCC 6227b)
Pellicularia filamentosa (ATCC 13 289)
Diplodia matalensis (ATCC 9055)
Rhizopus oryzae (ATCC 4858)
Rhizopus kazanensis (ATCC 8998)
Rhizopus cohuii (ATCC 8996)
Rhizopus shanghaiensis (ATCC 10 329)
Rhizopus stolonifer (ATCC 10 404)

The fermentation is conducted under the same conditions utilized in the conventional fermentative conversions of steriods with fungal cultures. Preferably the fermentative hydroxylation of the compounds of general Formula III is conducted in submerged cultures of the above-mentioned strains under aerobic conditions. For this purpose, the fungal cultures are incubated under aeration in a nutrient medium containing the carbohydrates, proteins, nutrient salts, and growing agents required for the growth of the fungi. After the incubation period is completed, the cultures are combined with the substrate as an aqueous suspension or in a suitable solvent, such as methanol, ethanol, glycol monomethyl ether, dimethylformamide, or dimethyl sulfoxide, and the fermentation is carried out until the reaction is terminated. The conversion of the substrate is controlled suitably by the analysis of sample extracts by thinlayer chromatography. As in all known microbiological conversions of steriods, the optimum substrate concentration and the optimum fermentation period in the process of this invention depend on the specific structure of the substrate and one the fermentation conditions proper and must be determined by means of the preliminary experiments familiar to a person skilled in the art.

After the fermentation has been completed, the fermentation products are isolated in a conventional manner. The isolation can be accomplished, for example, by extracting the fermentation batches with a polar, water-insoluble solvent, such as ethyl acetate, butyl acetate, or methyl isobutyl ketone, concentrating the extracts, and optionally purifying the thus-obtained crude products by chromatography and/or crystallization. Free hydroxy groups can subsequently be esterified or etherified. Esterified or etherified hydroxy groups can be converted into the free hydroxy groups.

The processes customarily employed in the steroid chemistry can be utilized for the esterification. Since the hydroxy groups in the 3-, 7-, and 17-positions have different reactivities, the hydroxy groups can be esterified stepwise. Depending on the selection of the reaction conditions, the thus-obtained products are the 3-mono-, 3,7-di-, or 3,7,17-triacyl compounds. The acylation in the 3- and 7-positions is preferably effected with pyridine/acid anhydride or with pyridine/acid halogenide at room temperature. If the acylation at a lower temperature is terminated after about 0.3 – 1 hour, the 3-monoacyl compound is obtained; in contrast thereto, if the acylation is continued over a period of several hours, the 3,7-diacyl compound is the result. In order to acylate the 17β-hydroxy group in 3,7-diacylates, the steroid is treated, for example, with acid anhydrides in the presence of strong acids, e.g. p-toluene-sulfonic acid or perchloric acid at room temperature or pyridine/acid anhydride under heating. These methods can also be employed to convert the free trihydroxy compound directly into the triacylate. From the triacylates, the 3-hydroxy group can be liberated by gentle partial saponification.

The trihydroxy compound, as well as the mono- and diesters, can be converted into the corresponding tetrahydropyranyl ethers with dihydropyran in the presence of a strong acid such as p-toluenesulfonic acid. From 3-monoacyl- or 3,7-diacyl-7, 17- or 17-tetrahydropyranyl ethers, the 3- or 3,7-hydroxy groups, respectively, can be liberated by alkaline saponification.

The cleavage of tetrahydropyranyl ethers takes place under mild conditions with the adddition of an acid, e.g. oxalic acid, in methylene chloride and methanol under boiling.

The etherification with an alkyl or cycloalkyl residue in the 3-position is preferably carried out with a corresponding halogenide in the presence of a weak base, such as potassium carbonate, sodium carbonate, etc. in an alcoholic solution at the boiling temperature, or with (cyclo-) alkyl halogenide in the presence of a strong base, such as sodium hydride, at room temperature.

Compounds etherified in the 3-position can subsequently be esterified in the 7-position and 17-position with carboxylic acids or can be reacted with dihydropyran.

A compound monoacylated in the 3-position with a carboxylic acid can be converted into the 7-sulfonic acid ester by conventionally reacting the 3-monoacyl compound in the presence of a tertiary amine with a sulfonic acid halogenide at room temperature. Analogously, a compound etherified in the 3-position can be sulfonylated in the 7-position.

If a trihydroxy compound is reacted with a sulfonic acid halogenide in the presence of a tertiary amine at room temperature, the 3,7-disulfonic acid ester is obtained. In case of the reaction with methanesulfonic acid chloride, it is advantageous to block the 17-hydroxy group, for example, by conversion into the 17-tetrahydropyranyl ether, for a hydroxy group which is not blocked in the 17-position can readily be split off by the methanesulfonyl chloride. Besides, it is advantageous in such a case to operate at temperatures of about $-10°$ to $+15°$ C.

The 3,7-dihydroxy-17-tetrahydropyranyl ether is prepared by converting the 3,7-diacyl compound, obtained with acid anhydride or halide in pyridine at room temperature, into the corresponding 17-tetrahydropyranyl ether with dihydropyran in the presence of a strong acid, such as p-toluene-sulfonic acid, and liberating the hydroxy groups in the 3- and 7-positions by alkaline saponification.

To produce a 3-monosulfonic acid ester, a 3-hydroxy-7,17-bis(tetrahydropyranyl ether) is reacted at room temperature with a sulfonic acid halgenide in the presence of a tertiary amine. The 3-hydroxy-7,17-bis(tetrahydropyranyl ether) is prepared, for example, by reacting the 3-monoacyl compound with dihydropyran and then effecting an alkaline saponification of the ester group in the 3-position.

Without further elaboration, it is believed that one skilld in the art can, using the preceding description, utilize the present invention to its fullest extent. The following preferred specific embodiments are, therefore, to be construed as merely illustrative, and not limitative, of the remainder of the disclosure in any way whatsoever.

EXAMPLE 1

(Microbiological 7α-Hydroxylation)

A 2-liter Erlenmeyer flask containing 500 ml. of a nutrient solution sterilized at 120° C. in an autoclave for 30 minutes, made of 3% glucose, 1% corn steep, 0.2% $NaNO_3$, 0.1% $KH_2PO_4$, 0.2% $K_2HPO_4$, 0.05% $MgSO_4$, 0.002% $FeSO_4$, and 0.05% KC1 is inoculated with a lyophilized culture of *Diplodia natalensis* (ATCC 9055) and incubated on a rotary shaker for 72 hours at 30° C. By means of this subculture, a 20-liter fermentor is then inoculated, this fermentor having been filled with 15 liters of a medium, sterilized at 121° C. and 1.1 atm. gauge, having the same composition as the subculture. While adding "Silicone SH" (dimethylpolysiloxane) as the defrother, the culture is germinated at 29° C. under aeration (10 liter/minute), 0.7 atm. gauge pressure, and agitation (220 r.p.m.) for 24 hours. One liter of the culture broth is transferred under sterile conditions into 14 liters of a nutrient medium sterilized as described above and having the same composition, and grown under identical conditions. After 12 hours, a sterile-filtered solution of 3 g. of ethynylestradiol in 100 ml. of dimethyl sulfoxide is added thereto.

The process of the conversion is observed by analyzing the methyl isobutyl ketone extracts of fermentor samples by thin-layer chromatography. After the conversion has been completed (45 hours contact period), the content of the fermentor is extracted twice with respectively 10 liters of methyl isobutyl ketone, and the extract is evaporated under vacuum at a bath temperature of 50° C.

The residue is taken up in methanol in order to remove the defrother; the silicone oil is separated by means of a separatory funnel, the solution is then filtered through a folded filter and again evaporated to dryness. The remaining crude product is now dissolved in methylene chloride and chromatographed for purification purposes over a silica gel column by means of a solvent gradient of methylene chloridemethylene chloride/acetone. After crystallization from ethyl acetate, the pure, white 17α-ethynyl-1,3,5(10)-estratriene-3,7α,17β-triol melts at 234°–235° C. (decomposition). $C_{20}H_{24}O_3$ (MW 312.4).

EXAMPLE 2

500 mg. of 17α-ethynyl-1,3,5(10)-estratriene-3,7α,17β-triol is dissolved in 10 ml. of pyridine; 0.5 ml. of acetic anhydride is added thereto, and the mixture is stirred for 20 minutes under ice cooling. Thereafter, the solution is stirred into 100 ml. of cooled 8% sulfuric acid, and the thus-produced precipitate is washed neutral. After drying, the product is recrystallized from ether/hexane, thus obtaining pure 3-acetoxy-17αethynyl-1,3,5(10)-estratriene-7α,17β-diol m.p. 133°–135° C.

EXAMPLE 3

At −10° C., acetylene is bubbled for 1 hour through a suspension of 3.7 g. of potassium tert.-butylate in 20 ml. of absolute tetrahydrofuran (THF). Under agitation, a solution of 500 mg. of 3,7α-dihydroxy-1,3,5(10)-estratrien-17-one, dissolved in 45 ml. of absolute THF, is added dropwise at −10° C. to the thus-obtained viscous mass. Acetylene is introduced for another hour, and the mixture is then stirred for ½ hour. To work up the reaction mixture, the latter is introduced into dilute cold acetic acid (saturated with NaCl), the substance is extracted with ethyl acetate, and the organic phase is washed neutral with sodium chloride solution. The crude product (630 mg.) is recrystallized from acetone/hexane over carbon, yielding 474 mg. of 17α-ethynyl-1,3,5(10)-estratriene-3,7α,17β-triol, m.p. 230°–232° C.

EXAMPLE 4

A solution of 100 mg. of 17α-ethynyl-1,3,5(10)-estratriene-3,7α,17β-triol in 5 ml. of ethyl acetate is combined at room temperature in succession with 1 ml. of acetic anhydride and 1 drop of perchloric acid (70% strength). After 3 minutes, 1 drop of pyridine is added; the mixture is washed with saturated sodium chloride solution, dried, and evaporated, thus obtaining 78 mg. of 3,7α,17β-triacetoxy-17α-ethynyl-1,3,5(10)-estratriene as an amorphous substance. With the use of enanthic anhydride in place of acetic anhydride, 3,7α,17β-tris(heptanoyloxy)-17α-ethynyl-1,3,5(10) estratriene is produced.

EXAMPLE 5

One milliliter of acetic anhydride is added to a solution of 150 mg. of 17α-ethynyl-1,3,5(10)-estratriene-3,7α,17β-triol in 3 ml. of pyridine; the reaction mixture is allowed to stand at room temperature for 16 hours. Then, the reaction mixture is evaporated to dryness while adding cyclohexane or $CCl_4$. The residue is dissolved in ethyl acetate and washed with water. Drying and evaporation yield 120 mg. of a crude product which is purified by layer chromatography, thus producing 110 mg. of 3,7α-diacetoxy-17α-ethynyl-1,3,5(10)-estratrien-17β-ol, m.p. 165°–166° C.

EXAMPLE 6

200 mg. of 17α-ethynyl-1,3,5(10)-estratriene-3,7α,17β-triol is dissolved in 3 ml. of methanol and 1 ml. of cyclopentyl bromide under heating; then, 200 mg. of potassium carbonate is added thereto and the mixture heated for 12 hours to the boiling point under a nitrogen atmosphere. The mixture is thereafter introduced into dilute cold acetic acid and extracted with methylene chloride. The organic phase is washed neutral, dried, and evaporated. The crude product (150 mg.) is purified by thin-layer chromatography, thus obtaining 110 mg. of 17α-ethynyl-3cyclopentoxy-1,3,5(10)-estratriene-7α,17β-diol, m.p. 126°–128° C.

EXAMPLE 7

A solution of 350 mg. of 17α-ethynyl-3-cyclopentoxy-1,3,5(10-estratriene-7α,17β-diol in 5 ml. of ethyl acetate is combined with 1 ml. of acetic anhydride and 1 drop of perchloric acid (70% strength) and agitated for 3 minutes at room temperature. Then, 0.5 ml. of pyridine is added thereto, and the mixture is washed with saturated sodium chloride solution, dried, and concentrated by evaporation, yielding 310 mg. of 7α,17β-diacetoxy-17α-ethynyl-3-cyclopentoxy-1,3,5(10)-estratriene as an amorphous substance.

UV (methanol): $\epsilon_{222} = 9060$; $\epsilon_{227} = 8730$; $\epsilon_{274} = 1460$; $\epsilon_{280} = 1920$; $\epsilon_{288} = 1770$.

EXAMPLE 8

Analogously to Example 3, 600 mg. of 3,7β-dihydroxy-1,3,5(10)-estratrien-17-one is reacted with acetylene to obtain 420 mg. of 17α-ethynyl-1,3,5(10)-estratriene-3,7β,17β-triol, m.p. 249° C.

EXAMPLE 9

Analogously to Example 4, 17α-ethynyl-1,3,5(10)-estratriene-3,7β,17β-triol is acetylated to produce 3,7β, 17β-triacetoxy-17α-ethynyl-1,3,5(10)-estratriene as an amorphous substance.

UV (methanol): $\epsilon_{210} = 9730$; $\epsilon_{264} = 709$; $\epsilon_{259} = 538$; $\epsilon_{271} = 694$.

EXAMPLE 10

Analogously to Example 6, 17α-ethynyl- 1,3,5(10)-estratriene-3,7β,17β-triol is etherified with cyclopentyl bromide to obtain 17α-ethynyl-3-cyclopentoxy-1,3,5(10)-estratriene- 7β,17β-diol; the substance is characterized after acetylation.

EXAMPLE 11

Analogously to Example 7, 17α-ethynyl-3-cyclopentoxy-1,3,5(10)-estratriene-7β,17β-diol is acetylated to 7β,17β-diacetoxy-17α-ethynyl-3-cyclopentoxy-1,3,5(10)-estratriene.

The substance is oily; UV (methanol): $\epsilon_{221} = 9030$; $\epsilon_{228} = 8710$; $\epsilon_{271} = 1450$; $\epsilon_{279} = 1910$; $\epsilon_{286} = 1750$.

EXAMPLE 12

500 mg. of 17α-ethynyl-1,3,5(10)-estratriene-3,7α,17β-triol is dissolved in 10 ml. of pyridine; 1 ml. of butyric anhydride is added thereto and the mixture agitated for 60 minutes at room temperature. Then, the solution is added to 100 ml. of cooled 8% sulfuric acid, and the thus-obtained precipitate is washed neutral. After drying, the product is recrystallized from ether/hexane, thus producing pure 3-butyryloxy-17α-ethynyl-1,3,5(10)-estratriene-7α,17β-diol, m.p. 130°–131° C.

EXAMPLE 13

500 mg. of 17α-ethynyl-1,3,5(10)-estratriene-3,7α,17β-triol is dissolved in 10 ml. of pyridine; 3 ml. of butyric anhydride is added thereto and the mixture stirred for 72 hours at room temperature. Thereafter, the solution is stirred into 100 ml. of cooled 8% sulfuric acid, and the thus-produced precipitate is washed with water until neutral. To further purify the product, it is chromatographed over a silica gel column and recrystallized from ether/hexane, producing the pure 3,7α-dibutyryloxy-17α-ethynyl-1,3,5(10)-estratrien-17β-ol, melting at 132.5° – 133° C.

EXAMPLE 14

(a) A suspension of 500 mg. of 3,7α-dihydroxy-1,3,5(10)-estratrien-17-one in 20 ml. of benzene is dried azeotropically by concentration to 10–15 ml. After cooling to room temperature, there are added in succession 1.1 ml. of dihydropyran and 5.4 mg. of p-toluenesulfonic acid (dehydrated azeotropically by distilling off benzene); under $N_2$, the mixture is agitated for 2.5 hours at room temperature. After the reaction is terminated, 1 drop of pyridine is added; the solution is washed neutral with sodium bicarbonate solution and water, dried, and evaporated, thus obtaining 750 mg. of 3,7α-bis-tetrahydropyranyloxy-1,3,5(10)-estratrien-17-one as an oil; which is used in the subsequent reaction (b) without any further purification.

(b) A lithium methyl solution is produced from 1.35 g. of lithium and 7.9 ml. of methyl iodide in 75 ml. of absolute ether. This solution is combined with 3.75 ml. of dichloroethylene in 15 ml. of absolute ether; the mixture is stirred for 1.5 hours at room temperature. This lithium chloroacetylene solution is then combined with 600 mg. of 3,7α-bis-tetrahydropyranyloxy-1,3,5(10)-estratrien-17-one in 30 ml. of absolute tetrahydrofuran, this latter mixture being added dropwise. The mixture is stirred for one hour at room temperature and for one hour at the reflux temperature. Thereafter the mixture is cooled off and decomposed under ice cooling with saturated sodium chloride solution. The organic phase is washed neutral with water, dried, and evaporated, thus obtaining 240 mg. of 3,7α-bis-tetrahydropyranyloxy-17α-chloroethynyl-1,3,5(10)-estratrien-17β-ol as an oily compound which is identical to the product of Example 15 after cleavage of the ether groups.

EXAMPLE 15

A solution of 200 mg. of 3,7α-bis-tetrahydropyranyloxy-17α-chloroethynyl-1,3,5(10-estratrien-17β-ol, 500 mg. of oxalic acid in 10 ml. of methanol, 5 ml. of methylene chloride, and 5 ml. of water is heated to boiling for 1 hour. Then, the mixture is diluted with ethyl acetate and washed neutral with saturated sodium chloride solution. Drying and evaporation yield 150 mg. of 17α-chloroethynyl-1,3,5(10)-estratriene-3,7α,17β-triol, m.p. 209°–221° C. (under decomposition).

EXAMPLE 16

(a) A solution of 250 mg. of 3,7α-dihydroxy-1,3,5(10)-estratrien-17-one in 1 ml. of dimethyl sulfoxide is combined under cooling and agitation with 250 mg. of sodium hydride (50% suspension in paraffin oil) and agitated for 30 minutes under nitrogen at room temperature. Then, 0.57 ml. of cyclopentyl bromide is added to the reaction mixture and the latter agitated for another 1.5 hours at room temperature under nitrogen. The mixture is then introduced into cold dilute acetic acid, filtered, and the precipitate taken up in ethyl acetate. After the reaction mixture has been washed neutral, dried, and evaporated, a crude product is obtained which is purified by means of column chromatography, thus producing 200 mg. of 3-cyclopentoxy-7α-hydroxy-1,3,5(10)-estratrien-17-one.

(b) For purposes of ethynylation, acetylene is passed for one hour through a suspension of 1.5 g. of potassium tert.butylate in 10 ml. of absolute THF. A solution of 200 mg. of 3-cyclopentoxy-7α-hydroxy-1,3,5(10)-estratrien-17-one in 20 ml. of absolute THF is added dropwise to the thus-produced pasty mixture at −10° C. under agitation. Acetylene is introduced for 1 hour and the mixture is then stirred for ½ hour. To work this mixture up, the latter is introduced into dilute cold acetic acids, extracted with ethyl acetate, and the organic phase washed neutral with sodium chloride solution. Drying, evaporation, and purification by chromatography produce 110 mg. of 17α-ethynyl-3-cyclopentoxy-1,3,5(10)-estratriene-7α,17β-diol, m.p. 126°–128° C.

EXAMPLE 17

At room temperature, 7 ml. of triethylamine and — under vigorous agitation — 1.4 ml. of isopropylsulfonic acid chloride are added to a solution of 450 mg. of 3-acetoxy-17α-ethynyl -1,3,5(10)-estratriene-7α,17β-diol in 30 ml. of absolute benzene; the mixture is agitated for 48 hours at room temperature. Then, the mixture is poured onto ice and the compound is extracted with ether. The ether phase is washed, dried, and evaporated, and the crude product is purified by gradient chromatography, thus obtaining 250 mg. of 17α-ethynyl-3-acetoxy-7α-isopropylsulfonyloxy-1,3,5(10)-estratrien-17β-ol.

EXAMPLE 18

A solution of 350 mg. of 17α-ethynyl-1,3,5(10)-estratriene-3,7α,17β-triol in 35 ml. of absolute benzene is combined at room temperature with 5 ml. of triethylamine and, under vigorous agitation, with 2 ml. of isopropylsulfonic acid chloride. The mixture is agitated for 38 hours at room temperature, then poured on ice, and extracted with ether. The ether phase is washed with water, dried, and concentrated by evaporation. The crude product is purified by gradient chromatography, thus obtaining 125 mg. of 17α-ethynyl-3,7α-bis-isopropylsulfonyloxy-1,3,5(10)-estratrien-17β-ol.

EXAMPLE 19

(a) A solution of 350 mg. of 3,7α-diacetoxy-17α-ethynyl-1,3,5(10)-estratrien-17β-ol in 20 ml. of absolute benzene is combined with 20 mg. of p-toluenesulfonic acid and 1 ml. of dihydropyran. The mixture is stirred overnight at room temperature, diluted with ether, washed with sodium bicarbonate solution and water until the mixture is neutral, and the latter is then evaporated, thus obtaining 300 mg. of 3,7α-diacetoxy-17α-ethynyl-17β-tetrahydropyranyloxy-1,3,5(10)-estratriene.

(b) 250 mg. of 3,7β-diacetoxy-17α-ethynyl-17β-tetrahydropyranyloxy1,3,5(10)-estratriene is dissolved in 10 ml. of methanol; a solution of 200 mg. of potassium carbonate in 2 ml. of water is added thereto, and the mixture is heated under nitrogen for 1.5 hours to the boiling point. Thereafter, the charge is introduced into ice water, and the organic compound is extracted with ether. After washing with water, drying, and evaporation, 180 mg. of 17α-ethynyl-17β-tetrahydropyranyloxy-1,3,5(10)-estratriene-3,7α-diol is obtained.

(c) Under ice cooling and nitrogen, 0.5 ml. of methanesulfonic acid chloride is added to a solution of 230 mg. of 17α-ethynyl-17β-tetrahydropyranyloxy-1,3,5(10)-estratriene-3,7α-diol in 5 ml. of pyridine; the mixture is stirred for 48 hours under nitrogen at about 4° C. Thereafter the mixture is introduced into ice water, the precipitate is filtered off and dissolved in methylene chloride, and after washing with water, drying, and evaporation, the product is 200 mg. of 17α-ethynyl-3,7α-bis-mesyloxy-17β-tetrahydropyranyloxy-1,3,5(10)-estratriene as a crude product which is further processed without any purification.

EXAMPLE 20

A solution of 200 mg. of 17α-ethynyl-3,7α-bis-mesyloxy-17β-tetrahydropyranyloxy-1,3,5(10)-estratriene in 5 ml. of methanol is combined with 500 mg. of oxalic acid, dissolved in 2 ml. of water. The mixture is heated to boiling for ½ hour, then introduced into ice water, and the organic substance is extracted with methylene chloride. After washing with water, drying, and evaporation, the product is 17α-ethynyl-3,7α-bis-mesyloxy-1,3,5(10)-estratrien-17β-ol.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A hydroxyestradiol of the formula

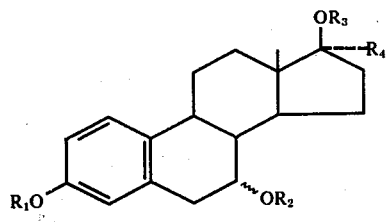

wherein $R_1$ is a hydrogen atom, the acyl radical of a hydrocarbon carboxylic or sulfonic acid of 1–15 carbon atoms, alkyl of 1–8 carbon atoms, cycloalkyl of 3–7 carbon atoms, tetrahydrofuranyl or tetrahydropyranyl;

$R_2$ and $R_3$ each are a hydrogen atom, the acyl radical of a hydrocarbon carboxylic or sulfonic acid of 1–15 carbon atoms, tetrahydrofuranyl or tetrahydropyranyl; and $R_4$ is alkenyl, chloroalkenyl, alkynyl or chloroalkynyl, each of up to 5 carbon atoms.

2. A compound of claim 1, wherein $R_1$, $R_2$ and $R_3$ each are hydrogen or alkanoyl of 1–7 carbon atoms, the 7-oxygen atom is in the α-position and $R_4$ is vinyl, ethynyl or chloroethynyl.

3. A compound of claim 1, wherein $R_1$, $R_2$ and $R_3$ each are hydrogen or alkanoyl of 1–7 carbon atoms, the 7-oxygen atom is in the β-position and $R_4$ is vinyl, ethynyl or chloroethynyl.

4. A compound of claim 1, wherein $R_1$ is cycloalkyl of 3–8 carbon atoms, $R_2$ and $R_3$ each are hydrogen or alkanoyl of 1–7 carbon atoms and $R_4$ is vinyl, ethynyl or chloroethynyl.

5. A compound of claim 1, wherein $R_1$ and $R_2$ each are hydrogen, tetrahydropyranyl or tetrahydrofuryl, $R_3$ is hydrogen or alkanoyl of 1–7 carbon atoms and $R_4$ is vinyl, ethynyl or chloroethynyl.

6. A compound of claim 1, wherein $R_1$ and $R_2$ each are hydrogen, alkanoyl of 1–7 carbon atoms or alkanesulfonyl of 1–4 carbon atoms; $R_3$ is hydrogen, alkanoyl of 1–7 carbons, tetrahydrofuryl or tetrahydropyranyl; and $R_4$ is vinyl, ethynyl or chloroethynyl.

7. A compound of claim 1, wherein $R_1$ is hydrogen or alkyl of 1–5 carbon atoms and $R_4$ is vinyl, ethynyl or chloroethynyl.

8. 17α-Ethynyl-1,3,5(10)-estratriene-3,7α,17β-triol, a compound of claim 1.

9. 3-Acetoxy-17α-ethynyl-1,3,5(10)-estratriene-7α,17β-diol, a compound of claim 1.

10. 3,7α,17β-Triacetoxy-17α-ethynyl-1,3,5(10)-estratriene, a compound of claim 1.

11. 3,7α-Diacetoxy-17α-ethynyl-1,3,5(10)-estratrien-17β-ol, a compound of claim 1.

12. 17α-Ethynyl-3-cyclopentoxy-1,3,5(10)-estratriene-7α,17β-diol, a compound of claim 1.

13. 7α,17β-Diacetoxy-17α-ethynyl-3-cyclopentoxy-1,3,5(10)-estratriene, a compound of claim 1.

14. 17α-Ethynyl-1,3,5(10)-estratriene-3,7β,17β-triol, a compound of claim 1.

15. 3,7β,17β-Triacetoxy-17α-ethynyl-1,3,5(10)-estratriene, a compound of claim 1.

16. 17α-Ethynyl-3-cyclopentoxy-1,3,5(10)-estratriene-7β,17β-diol, a compound of claim 1.

17. 7β,17β-Diacetoxy-17α-ethynyl-3-cyclopentoxy-1,3,5(10)-estratriene, a compound of claim 1.

18. 3-Butyryloxy-17α-ethynyl-1,3,5(10)-estratriene-7α,17β-diol, a compound of claim 1.

19. 3,7α-Dibutyryloxy-17α-ethynyl-1,3,5(10)-estratrien-17β-ol, a compound of claim 1.

20. 3,7α-Bis-tetrahydropyranyloxy-17α-chloroethynyl-1,3,5(10)-estratrien-17β-ol, a compound of claim 1.

21. 17α-Chloroethynyl-1,3,5(10)-estratriene-3,7α,17β-triol, a compound of claim 1.

22. 17α-Ethynyl-3-acetoxy-7α-isopropylsulfonyloxy-1,3,5(10)-estratrien-17βol, a compound of claim 1.

23. 17α-Ethynyl-3,7α-bis-isopropylsulfonyloxy-1,3,5(10)-estratrien-17βol, a compound of claim 1.

24. 17α-Ethynyl-3,7α-bis-mexyloxy-17β-tetrahydropyranyloxy-1,3,5(10)-estratrien, a compound of claim 1.

25. 17α-Ethynyl-3,7α-bis-mexyloxy-1,3,5(10)-estratrien-17β-ol, a compound of claim 1.

26. A pharmaceutical composition comprising an estrogenic amount per unit dosage of a compound of claim 1 in a pharmaceutically effective carrier.

27. 3,7α,17β-Tris(heptanoyloxy)-L7α-ethynyl-1,3,5(10)-estratriene, a compound of claim 1.

28. A method of treating estrogen deficiency syndromes in a female mammal which comprises the enteral or parenteral administration of an amount effective to ameliorate symptoms of estrogen deficiency in the female mammal of a hydroxyestradiol of the formula.

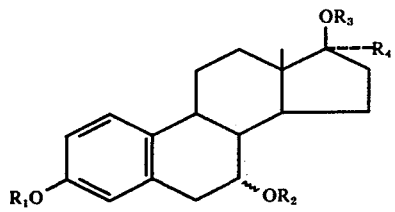

wherein $R_1$ is a hydrogen atom, the acyl radical of a hydrocarbon carboxylic or sulfonic acid of 1–15 carbon atoms, alkyl of 1–8 carbon atoms, cycloalkyl of 3–7 carbon atoms, tetrahydrofuranyl or tetrahydropyranyl; $R_2$ and $R_3$ each are a hydrogen atom, the acyl radical of a hydrocarbon carboxylic or sulfonic acid of 1–15 carbon atoms, tetrahydrofuranyl or tetrahydropyranyl and $R_4$ is alky, alkenyl, chloroalkenyl, alkynyl or chloroalkynyl, each of up to 5 carbon atoms.

* * * * *